United States Patent
Krueger

(10) Patent No.: US 7,189,252 B2
(45) Date of Patent: Mar. 13, 2007

(54) WARMING/CHILLING APPARATUS

(75) Inventor: Bernd Krueger, Nienburg (DE)

(73) Assignee: Krueger & Gothe GmbH, Stassfurt (DE)

( * ) Notice: Subject to any disclaimer, the term of this patent is extended or adjusted under 35 U.S.C. 154(b) by 95 days.

(21) Appl. No.: 10/808,969

(22) Filed: Mar. 25, 2004

(65) Prior Publication Data

US 2004/0193237 A1    Sep. 30, 2004

(30) Foreign Application Priority Data

Mar. 25, 2003   (DE) .............................. 103 14 138

(51) Int. Cl.
   *A61F 7/00*   (2006.01)
(52) U.S. Cl. ..................... 607/104; 607/108
(58) Field of Classification Search ............... 606/24, 606/27–41; 435/286.1, 287.1; 702/130, 702/132; 607/96, 104, 105, 108–111
   See application file for complete search history.

(56) References Cited

U.S. PATENT DOCUMENTS

| | | | |
|---|---|---|---|
| 3,207,159 A | | 9/1965 | Tateisi et al. |
| 3,289,749 A | * | 12/1966 | Crump ...................... 165/48.1 |
| 3,618,590 A | | 11/1971 | Yardley et al. |
| 4,585,002 A | | 4/1986 | Kissin |
| 4,653,507 A | | 3/1987 | Laudadio |
| 4,741,338 A | | 5/1988 | Miyamae |
| 4,763,666 A | | 8/1988 | Strian et al. |
| 4,860,748 A | | 8/1989 | Chiurco et al. |
| 5,653,741 A | * | 8/1997 | Grant ........................ 607/114 |
| 5,746,702 A | | 5/1998 | Gelfgat et al. |
| 6,228,634 B1 | * | 5/2001 | Blumenfeld et al. ...... 435/286.1 |
| 6,556,940 B1 | * | 4/2003 | Tretiakov et al. .......... 702/130 |
| 6,776,779 B1 | * | 8/2004 | Roy et al. ..................... 606/28 |
| 2002/0107543 A1 | | 8/2002 | Hollander et al. |

FOREIGN PATENT DOCUMENTS

| | | |
|---|---|---|
| DE | 100 65 592 | 7/2002 |
| DE | 101 47 563 | 4/2003 |
| EP | 0 330 472 | 8/1989 |
| WO | WO 02/064069 | 8/2002 |

OTHER PUBLICATIONS

Data sheet: Minco Thermofoil Heaters.*

* cited by examiner

*Primary Examiner*—Roy D. Gibson
(74) *Attorney, Agent, or Firm*—Akerman & Senterfit; Stephan Pendorf

(57) ABSTRACT

A warming/chilling apparatus, in particular for a pain treatment unit, includes a heating device and a cooling device for alternately heating and cooling a heating/cooling element to a high and a low tempemture respectively. The heating device and the cooling device are designed and arranged relative to each other in such a way that the change between the high and the low temperature is possible within three minutes and the temperature difference between the high and the low temperatures is at least 40° C.

15 Claims, 3 Drawing Sheets

WARMING/CHILLING APPARATUS

BACKGROUND OF THE INVENTION

1. Field of Invention

The present invention relates to a warming/chilling apparatus, in particular a warming/chilling apparatus for a pain treatment unit, comprising a heating device and a cooling device for alternately heating and cooling a heating/cooling element.

Pain such as for example migraine and tension headaches as well as tinnitus complaints and comparable complaints are frequently treated by drug administration. In past years however alternative approaches to the treatment of pain have also been developed. Some of those aim to eliminate or at least reduce pain by means of a warming/chilling treatment.

2. Related Art of the Invention

A method and an apparatus for carrying out a warming/chilling treatment are described in DE 100 65 592.

The method described in DE 100 65 592 is based on applying heat and cold to the patient on a rhythmically changing basis. Depending on the nature of the pain, the application of heat or cold respectively is effected over respectively identical or different periods of time. The heat or cold acts over a period of seconds or minutes before the procedure is switched over from hot to cold or from cold to hot.

The apparatus which is used to carry out that pain treatment has a headset with two earpieces. In one embodiment a warming element and a chilling element are arranged in mutually juxtaposed relationship in the earpiece. Controlled by a time interval control system, the apparatus provides for alternately applying the warming and the chilling element to the skin. The result of this however is that the heat and the cold are applied at different locations on the skin. In a further embodiment the heat and the cold are applied to the skin at the same location. For that purpose, a warming/chilling element with the possibility of accommodating fluid is arranged in the earpiece. Heating or cooling fluid is fed to the warming/chilling element by way of tubes in order to warm it or cool it. However, heating and cooling of the warming/chilling element requires a relatively long period of time, which is in conflict with a rapid change from warm to cold or vice-versa.

A further apparatus for the treatment of pain by means of the alternate supply of warmth and cold is known from U.S. Pat. No. 4,585,002. The zone of the body to be treated is alternately supplied with warmth and cold by means of Peltier elements. The temperatures range between 25° C. and 43° C. In that situation a control unit controls the flow of current to the Peltier elements in such a way that the change between warm and cold takes place several times per minute.

An apparatus for producing a series of temperature patterns for reducing pain is disclosed in EP 0 330 472. The temperatures are produced by means of thermoelectric elements and are in the range of between 19° and 44°. A change in the temperature gradient takes place at most once per minute.

U.S. Pat. No. 5,746,702 discloses an apparatus for skin massage. The massage effect is achieved by warmth and cold being supplied to the skin in a cyclic change procedure. The apparatus for performing the skin massage includes two treatment blocks which are pressed against the head of the person to be treated, by means of curved springs. A contact plate can be warmed to temperatures of between 25° C. and 32° C. and cooled to temperatures of between 10° C. and 17° C., by means of Peltier elements. For warming or cooling the contact plate, a pulse generator supplies the Peltier elements with bipolar current pulses of a duration of between 60 and 90 seconds.

SUMMARY OF THE INVENTION

In comparison with the above-quoted state of the art, the object of the present invention is to provide a warming/chilling apparatus which can advantageously be used in a unit for pain treatment.

A further object of the invention is to provide a pain treatment unit with a warming/chilling apparatus which is improved over the state of the art.

The first object is attained by a warming/chilling apparatus as set forth in claim 1 and the second object is attained by a pain treatment unit as set forth in claim 16.

The dependant claims set forth advantageous configurations of the invention.

A warming/chilling apparatus according to the invention, in particular for a pain treatment unit, includes a heating device and a cooling device for alternately heating and cooling a heating/cooling element to a high and a low temperature respectively. The heating device and the cooling device are designed and arranged relative to each other in such a way that the change between the high and the low temperature is possible within three minutes and the temperature difference between the high and the low temperatures is at least 40° C.

In this case the heating and the cooling devices can be in the form of devices for producing warmth or cold, or in the form of devices for transmitting warmth or cold respectively.

The invention is based on the insight that, in terms of treatment of pain, in particular when treating a migraine, good treatment results can be achieved if the patient is administered with temperature differences of at least 40° C. at relatively short time spacings, in particular time spacings of less than three minutes. Temperature differences of that kind cannot be achieved in such short periods of time, with the warming/chilling apparatuses known from the state of the art.

Advantageously, the high temperature is at least 50° C. and the low temperature is at most +10° C. It is particularly advantageous if the high temperature is between 50° C. and 60° C., in particular being 60° C., and the low temperature is between −20° C. and 0° C., in particular being −20° C. With the present invention it is in particular possible to produce temperature differences of up to 80° C., that is to say to change the treatment temperature by 80° C., within less than one minute, in particular in only 30 seconds, and that gives particularly good treatment results. In addition the warming/chilling apparatus according to the invention makes it possible to apply hot and cold to the same treatment location.

In an advantageous configuration of the invention, the heating/cooling element has a heating/cooling face, wherein the heating/cooling face includes at least one surface of the heating device or surface of the cooling device. In that way it is possible to provide for direct heating or cooling without the interposition of further elements which delay the heating or cooling operation.

In particular the heating/cooling face can be formed by a surface of the heating device. The cooling device is then arranged on the side of the heating device which is remote from the heating/cooling face. In addition the heating device has a low heat capacity. If the heating device is switched on during the heating phase, the surface thereof delivers heat to the region of the body to be treated. The cooling device can but does not have to be switched off during the heating period. During the cooling phase in which the heating device is switched off and the cooling device is switched on, the heating device rapidly loses its residual heat, by virtue of its low heat capacity, so that its surface can be rapidly cooled to the low temperature, by the cooling element.

In this embodiment the heating device can be in particular an electrical heating plate. The low heat capacity can be achieved for example by the heating plate being less than 0.5 mm in thickness. In a particularly advantageous configuration the thickness of the heating plate is about 0.1 mm. Instead of or in addition to a suitable choice for the thickness of the heating plate, a low heat capacity can also be achieved by a suitable choice of the material used.

A thermoelectric element, in particular a Peltier element, can be used as the cooling device. In addition, a cooling body can be arranged at the side of the thermoelectric element, that is remote from the heating device, for dissipating excess heat.

In an alternative configuration of the warming/chilling apparatus according to the invention, the heating device and the cooling device are so designed that the heating/cooling face is formed alternately by a surface of the heating device and a surface of the cooling device. That permits both direct heating and also direct cooling of the area of the body to be treated, without the need to interpose further elements which delay the heating or cooling operation.

In order to permit the change from the surface of the heating device as a heating/cooling face to the surface of the cooling device as a heating/cooling face, the heating device may include in particular tube-like portions for the flow of a heating fluid and the cooling device may include tube-like cooling portions for the flow of a cooling fluid, which are each made from an elastic material. In addition there is then at least one pressure producing means for alternately producing high and low fluid pressure in the heating fluid and the cooling fluid respectively, wherein the change of high and low fluid pressure is effected in such a way that the heating fluid is at a high fluid pressure while the cooling fluid is at a low fluid pressure and vice-versa. The tube-like heating portions and the tube-like cooling portions as well as the high fluid pressure and the low fluid pressure are in that case matched to each other in such a way that those tube-like portions in which the high fluid pressure prevails cover over the tube-like portions in which the low fluid pressure prevails.

In an advantageous development of that configuration the tube-like portions are arranged in mutually juxtaposed relationship on a common plate. The common plate provides that the tube-like portions can expand only in the direction remote from the plate. That ensures that the covering of the portions in which low fluid pressure prevails by those portions in which high fluid pressure prevails is only in one direction, namely in the direction of that side which is to be towards the part of the body to be treated.

A rubber-metal mixture is suitable as the material for the tube-like portions. In that case, the rubber ensures elasticity and the metal ensures thermal conductivity of the tube-like portions.

The warming/chilling apparatus according to the invention is not only suitable for use in the treatment of pain, for example the treatment of migraine. It is also possible to envisage uses in other areas in which temperature differences of 40° C. with the same absolute temperatures as in the treatment of pain are to be applied to an object, within short periods of time.

A pain treatment unit according to the invention is provided with a warming/chilling apparatus according to the invention. A pain treatment unit of such a configuration permits pain and in particular migraine to be effectively treated.

BRIEF DESCRIPTION OF THE DRAWINGS

Further features, properties and advantages of the present invention are described hereinafter by means of embodiments by way of example with reference to the accompanying drawings in which.

DETAILED DESCRIPTION OF THE INVENTION

Figure 1:
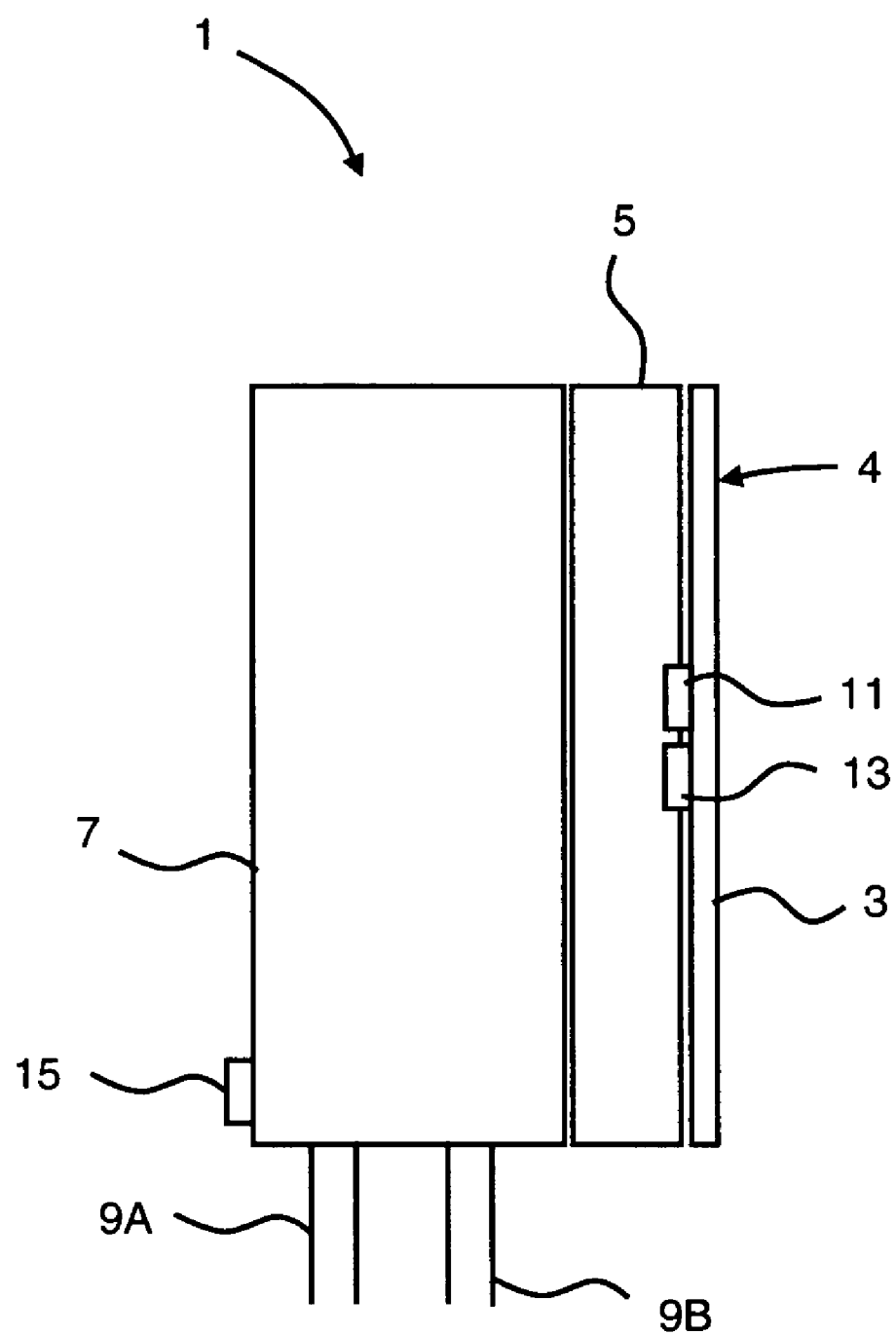
FIG. 1 shows a first embodiment of a warming/chilling apparatus according to the invention.

A first embodiment of the present invention is shown in FIG. 1. The heating/cooling element 1 which is shown in FIG. 1 and which is used as a heating/cooling element in a pain treatment unit includes an electrical heating plate 3 as a heating device and a Peltier element 5 as a cooling device. It can be integrated into an earpiece which is fixed in the manner of a headset to the end of a band which is to be worn on the head. Advantageously, the band includes two such earpieces, one at each respective end of the band. Alternatively the heating/cooling element 1 can also be fixed to a band which is to be worn on the body. Examples in regard to the design configuration of such an earpiece or such a band are described for example in DE 100 65 592.

Instead of the heating/cooling element 1 being integrated into an earpiece fixed to a band however, it can also be fixed directly to the band. Such a design configuration is to be found for example in U.S. Pat. No. 5,746,702.

Irrespective of whether the heating/cooling element 1 is arranged in an earpiece or fixed directly to the band, the band is preferably fitted to the patient in the treatment procedure in such a way that the heating/cooling elements 1 which are arranged at the ends of the band bear against the temples.

During the treatment, heating of the heating/cooling element 1 to values of between 50° C. and 60° C., in particular to 60° C., and cooling of the heating/cooling element 1 to values of between −20° C. and 0° C., in particular to −20° C., are effected in an alternately changing procedure. In that case, the heating plate 3 and the Peltier element 5 are alternately supplied with electrical power in such a way that the temperature change from +60° C. to −20° C. takes place within 30 seconds. The temperature change which takes place so quickly is made possible by a specific structure for the heating/cooling element 1.

The surface 4 of the electrical heating plate 3 serves for applying the warmth or cold to the skin of the patient. It can be provided with an electrically insulating covering, for example a plastic covering. The covering however should have a high level of thermal conductivity in order not to have an adverse influence on the application of warmth or cold.

The electrical heating plate is of a thickness of 0.1 mm and involves an area of 40×40 mm and is made from a copper alloy, for example FX 9. By virtue of its small thickness, the heat capacity of the heating plate 3 is correspondingly low, which accelerates cooling-down thereof after the end of a heating phase. It has a low conductance of about 2 MS/m and, during the heating phase, a current of a strength of 30 A to 70 A flows therethrough. In the present embodiment the current strength is 65 A and the applied voltage is 0.5 V.

The electrical heating plate 3 is glued on to the Peltier element 5 by means of a thermally conductive adhesive. The cooling output is produced with the Peltier element during the cooling phase. The cooling output is very rapidly available, by virtue of the small thickness of the electrical heating plate 3. When current flows (in the present embodiment 5 A at 16 V) the Peltier element 5 produces cold on one side while as a counterpart heat is produced on the other side of the element. In order for that heat to be quickly dissipated, a water cooling body 7 is arranged on its side remote from the electrical heating plate 3. The water cooling body is connected to a closed water circuit, by way of which the excess heat is removed. FIG. 1 shows the feed conduit 9A and the discharge conduit 9B of the water circuit. Instead of water cooling, it is also possible to provide for air cooling if the amount of heat which is to be removed allows that. In that case, instead of a connection to a closed water circuit, the cooling body has cooling ribs for the air cooling effect.

Three temperature sensors 11, 13 and 15 monitor the variation in temperature during operation of the heating/cooling element 1. The temperature sensor 11 outputs its temperature signal to a control circuit while the temperature sensor 13 which monitors the maximum temperature values on the heating plate 3 and the temperature sensor 15 which monitors the temperature of the cooling body 7 deliver their temperature signals to a safety circuit. When predetermined safety values for the corresponding temperatures are exceeded, the safety circuit switches the unit to a fault condition and terminates operation.

Figure 2:
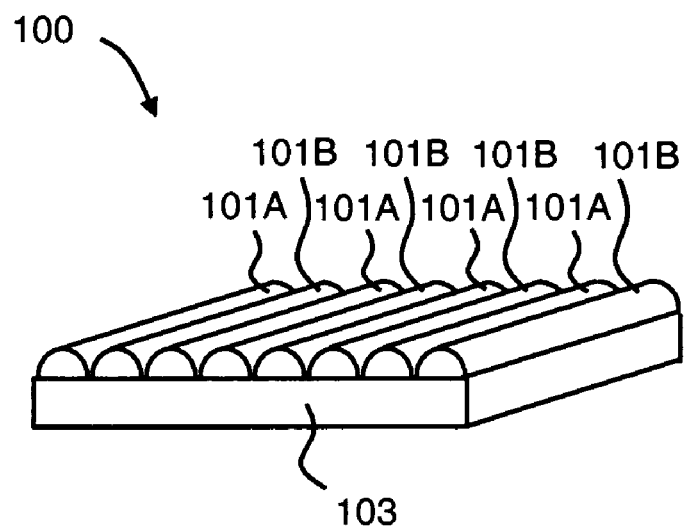
FIG. 2 shows a second embodiment of a warming/chilling apparatus in a first condition.
Figure 3:
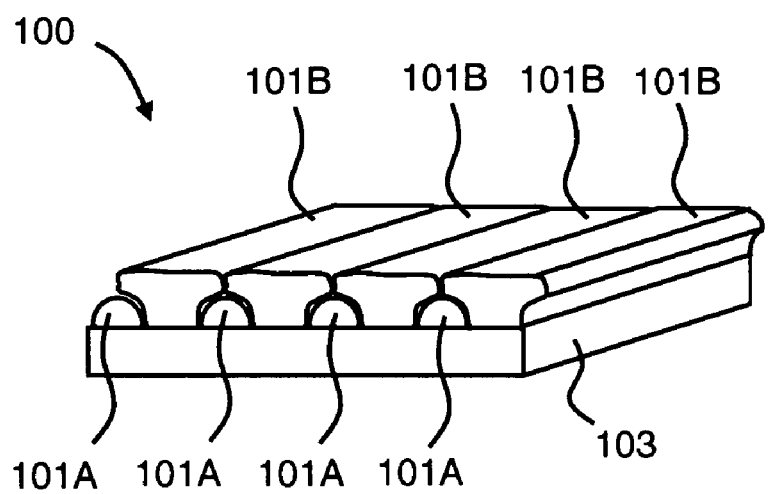
FIG. 3 shows a second embodiment of a warming/chilling apparatus in a second condition.
Figure 4:
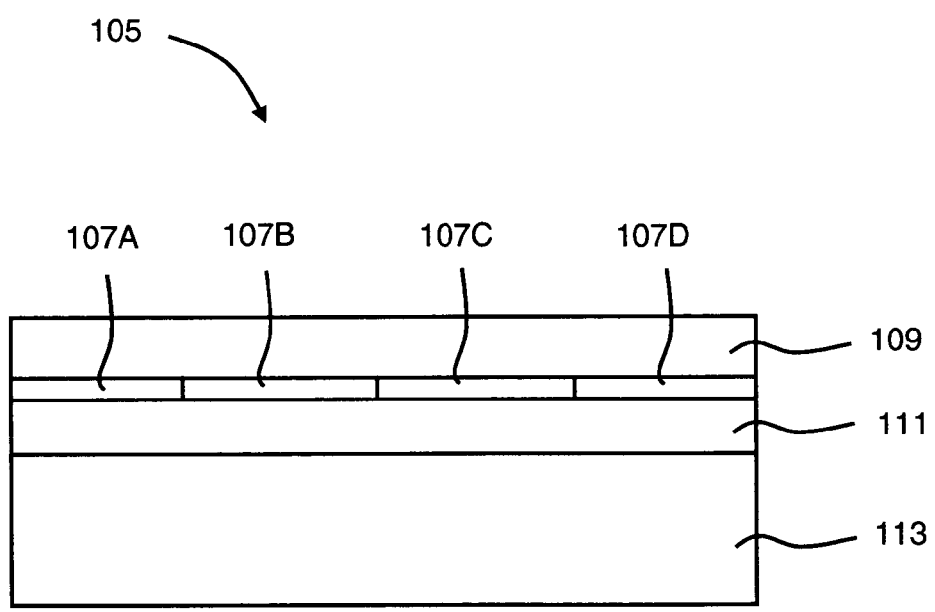
FIG. 4 shows the arrangement of thermoelectric elements in the second embodiment.

A second embodiment of the warming/chilling apparatus according to the invention is shown in FIGS. 2 to 4. In contrast to the embodiment shown in FIG. 1 the warmth or cold is not produced directly in the heating/cooling element 100 but is fed to the heating/cooling element 100 by means of a heating fluid and a cooling fluid. Preferably liquids, in particular oils or water, are used as the heating and cooling fluids respectively.

The heating/cooling element 100 is shown in FIGS. 2 and 3. It has a number of thin-wall, tube-like heating portions 101A which are arranged alternately with a number of also thin-wall and tube-like cooling portions 101B, on a rubber plate 103. The tube-like heating portions 101A are designed to receive the heating fluid during the heating phase and are of an elastic configuration while the tube-like cooling portions 101B are designed to receive the cooling fluid during the cooling phase and are also of an elastic configuration. By virtue of its elastic properties and its thermal conductivity, a rubber-metal mixture is suitable as the material for the tube-like heating and cooling portions 101A, 101B.

In the present embodiment, the tube-like heating portions 101A, together with the heating fluid, form the heating device while the tube-like cooling portions 101B, together with the cooling fluid, form the cooling device.

For heating the heating fluid and cooling the cooling fluid, the corresponding tube-like portions are connected by way of fluid conduits to a heating means and a cooling means 105 respectively. The fluids can be pumped into or out of their tube-like portions by means of a pump so that a high and a low fluid pressure obtains alternately in the portions. In that arrangement the pump is controlled in such a way that a high pressure obtains in the tube-like heating portions 101A when a low pressure obtains in the tube-like cooling portions 101B, and vice-versa.

In the illustrated embodiment the side, that is to be towards the patient, of the tube-like heating and cooling portions 101A, 101B respectively, is of a substantially semicircular cross-section (see FIG. 2), in the relaxed condition, that is to say in the condition of not being subjected to the effect of fluid pressure. The half, that is to face away from the patient, of the tube-like portions 101A, 101B, is formed by the rubber plate 103 which is about 2 mm in thickness.

During the heating phase the warming fluid is urged into the tube-like heating portions 101A so that those portions are subjected to the effect of a pressure. At the same time the chilling fluid is removed from the tube-like cooling portions 101B so that a low pressure obtains there. In that case, the thin tube-like heating portions 101A expand in such a way that they completely cover over the tube-like cooling portions 101B which, in the heating phase, are only of a small cross-section (FIG. 3). In that condition, the upper halves of the tube-like heating portions 101A form a substantially closed surface which serves as a heating face of the heating/cooling element 100.

During the cooling phase in contrast the chilling fluid is urged into the tube-like cooling portions 101B while the warming fluid is removed from the tube-like heating portions 101A. In that condition the cooling portions 101B expand in such a way that they cover over the heating portions 101A which in the cooling phase are only of a small cross-section, and they form a substantially closed cooling face of the heating/cooling element 100.

The rubber plate 103 which functions as a common rear side of the heating and cooling portions 101A, 101B prevents lateral displacement of the tube-like portions 101A, 101B upon being subjected to the effect of fluid pressure, and thereby ensure that the substantially closed surface is produced.

With this configuration also it is possible to vary the temperatures between 60° C. and −20° C., within 30 seconds.

FIG. 4 shows a combined heating/cooling arrangement 105 for heating the heating fluid and cooling the cooling fluid. The heating/cooling arrangement 105 includes a row of Peltier elements 107A–107D arranged between a fluid-filled cooling fluid body 109 and a fluid-filled heating fluid body 111.

The Peltier elements 107 are supplied with current in such a way that, when current flows, the side of the Peltier elements 107A–107D, that is towards the heating fluid body 111, is heated, and thus heats the heating fluid in the heating fluid body 111, while the side that is towards the cooling fluid body 109 cools down and cools the cooling fluid in the cooling fluid body 109. The warmed heating fluid and the cooled cooling fluid are pumped alternately into and out of the tube-like heating portions 101A and cooling portions 101B respectively by the pump by way of suitable fluid conduits, in operation of the apparatus.

For the purposes of removing excess heat which is not to be absorbed by the heating fluid, it is also possible to arrange on the heating fluid body 111 an air cooling body 113 which is equipped for example with cooling ribs.

The heating/cooling element 100 of the second embodiment, like that of the first embodiment, can be integrated in an earpiece fixed to a band, it can be fixed directly to a band, or it can be fixed to a band which is to be applied to the body.

The invention claimed is:

1. A warming/chilling apparatus comprising:
   a heating/cooling element, and
   a heating device and cooling device for alternately heating and cooling the heating/cooling element to a high and a low temperature respectively,
   wherein the heating device and the cooling device are designed and arranged relative to each other in such a way that the change between the high and the low temperature is possible within three minutes,
   wherein the temperature difference between the high and the low temperatures is at least 40° C.
   wherein the heating/cooling element has a heating/cooling face, and the heating/cooling face includes at least one surface of the heating device or surface of the cooling device, and
   wherein a surface of the heating device forms the heating/cooling face, the cooling device is attached on the side of the heating device, that is remote from the heating/cooling face, and the heating device has a low heat capacity.

2. The warming/chilling apparatus according to claim 1, wherein the high temperature is at least 50° C. and the low temperature is at most +10° C.

3. The warming/chilling apparatus according to claim 2 wherein the low temperature is less than 0° C.

4. The warming/chilling apparatus according to claim 1, wherein the heating device and the cooling device are designed and arranged relative to each other in such a way that a change between the high and the low temperatures is possible within a minute.

5. The warming/chilling apparatus according to claim 4, wherein the heating device and the cooling device are designed and arranged relative to each other in such a way that a change between the high and the low temperatures is possible within 30 seconds.

6. The warming/chilling apparatus according to claim 1, wherein the heating/cooling element has a heating/cooling face, and the heating/cooling face includes at least one surface of the heating device or surface of the cooling device.

7. The warming/chilling apparatus according to claim 1, wherein the heating device is an electrical heating plate.

8. The warming/chilling apparatus according to claim 7, wherein the thickness of the heating plate is less than 0.5 mm.

9. The warming/chilling apparatus according to claim 1, wherein the cooling device is a thermoelectric element.

10. The warming/chilling apparatus according to claim 9, wherein a cooling body for dissipating excess heat is arranged at the side of the thermoelectric element that is remote from the heating device.

11. A warming/chilling apparatus comprising:
    a heating/cooling element, and
    a heating device and cooling device for alternately heating and cooling the heating/cooling element to a high and a low temperature respectively,
    wherein the heating device and the cooling device are designed and arranged relative to each other in such a way that the change between the high and the low temperature is possible within three minutes,
    wherein the temperature difference between the high and the low temperatures is at least 40° C.
    wherein the heating/cooling element has a heating/cooling face, and the heating/cooling face includes at least one surface of the heating device or surface of the cooling device, and
    wherein the heating device and the cooling device are so designed that a surface of the heating device and a surface of the cooling device alternately form the heating/cooling face.

12. The warming/chilling apparatus according to claim 11, wherein the heating device includes tube-like portions for the flow of a heating fluid and the cooling device includes tube-like cooling portions for the flow of a cooling fluid, which are each made from an elastic material, and that there is at least one pressure producing means for alternately producing high and low fluid pressure in the heating fluid and the cooling fluid respectively, and wherein the change of high and low fluid pressure is effected in such a way that the heating fluid is at a high fluid pressure while the cooling fluid is at a low fluid pressure and vice-versa, and wherein the tube-like heating portions and the tube-like cooling portions as well as the high fluid pressure and the low fluid pressure are matched to each other in such a way that those tube-like portions in which the high fluid pressure prevails cover over the tube-like portions in which the low fluid pressure prevails.

13. The warming/chilling apparatus according to claim 12, wherein in that the tube-like portions are arranged in mutually juxtaposed relationship on a common plate.

14. The warming/chilling apparatus according to claim 12, wherein the tube-like portions comprise a rubber-metal mixture.

15. A pain treatment unit comprising a heating device and a cooling device for alternately heating and cooling a heating/cooling element to a high and a low temperature respectively, wherein
    the heating/cooling element comprises an electrical heating plate having a low heat capacity and a thickness less than 0.5 mm as the heating device, a surface of which forms a heating/cooling face of the heating/cooling element;
    the heating/cooling element comprises a thermoelectric element as the cooling device which is fixed by means of a thermally conductive adhesive to the side of the heating device, that is remote from the heating/cooling face; and
    the electrical heating plate and the thermoelectric element are driven such that a change between the high and the low temperature takes place within three minutes and that the temperature difference between the high and the low temperatures is at least 40° C.

* * * * *